US008779907B2

(12) United States Patent
Liu et al.

(10) Patent No.: US 8,779,907 B2
(45) Date of Patent: Jul. 15, 2014

(54) MULTIFUNCTIONAL SWITCH AND DETECTOR ASSEMBLY FOR A MEDICAL IMAGING SYSTEM INCLUDING THE SAME

(75) Inventors: James Zhengshe Liu, Glenview, IL (US); Scott William Petrick, Sussex, WI (US); Donald Fayette Langler, Brookfield, WI (US); Gary Vernon McBroom, Dousman, WI (US); Roy Allan Schley, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 1297 days.

(21) Appl. No.: 12/550,965

(22) Filed: Aug. 31, 2009

(65) Prior Publication Data
US 2011/0050403 A1    Mar. 3, 2011

(51) Int. Cl.
*G08B 23/00* (2006.01)
*G08B 21/00* (2006.01)
*G06F 1/32* (2006.01)
*A61B 6/00* (2006.01)
*A61B 8/00* (2006.01)
*A61B 5/055* (2006.01)

(52) U.S. Cl.
CPC .......... *A61B 6/56* (2013.01); *A61B 8/4405* (2013.01); *G06F 1/3206* (2013.01); *A61B 5/055* (2013.01); *A61B 8/00* (2013.01); *A61B 2560/0209* (2013.01); *A61B 6/4405* (2013.01); *A61B 6/467* (2013.01); *G06F 1/3287* (2013.01); *A61B 6/4233* (2013.01)
USPC .......................... 340/384.1; 340/500; 340/635

(58) Field of Classification Search
None
See application file for complete search history.

(56) References Cited

U.S. PATENT DOCUMENTS

| | | | |
|---|---|---|---|
| 4,965,726 A * | 10/1990 | Heuscher et al. | 378/19 |
| 5,065,434 A * | 11/1991 | Matsuoka et al. | 382/114 |
| 5,262,946 A * | 11/1993 | Heuscher | 378/15 |
| 5,693,948 A * | 12/1997 | Sayed et al. | 250/370.09 |
| 5,773,832 A | 6/1998 | Sayed et al. | |
| 6,173,031 B1 * | 1/2001 | Hoffman et al. | 378/19 |
| 6,448,561 B1 | 9/2002 | Kaifu | |
| 7,342,998 B2 | 3/2008 | Kump et al. | |
| 7,365,337 B2 | 4/2008 | Tsuchino et al. | |
| 7,429,737 B2 | 9/2008 | Wojcik et al. | |
| 7,488,946 B2 | 2/2009 | Hennessy et al. | |
| 7,583,779 B2 * | 9/2009 | Tkaczyk et al. | 378/4 |
| 7,713,229 B2 * | 5/2010 | Veit et al. | 604/65 |

(Continued)

FOREIGN PATENT DOCUMENTS

JP          2007333383 A       12/2007

OTHER PUBLICATIONS

Search Report and Written Opinion from FR Patent Application No. 1056730 dated Apr. 26, 2013.

(Continued)

*Primary Examiner* — Julie Lieu (57) ABSTRACT

A control circuit for a portable x-ray medical imaging system detector. The control circuit operates to reduce power consumption of the portable x-ray detector. The detector control circuit includes a multi-function switch coupled to the portable detector, and a detector control module installed in the portable detector, the detector control module receiving an input from the multi-function switch and based on the received input reconfiguring the portable detector from a first operational mode to a different second operational mode. A portable detector including the detector control circuit and a method of operating the portable detector are also provided.

17 Claims, 6 Drawing Sheets

(56) References Cited

U.S. PATENT DOCUMENTS

| | | | |
|---|---|---|---|
| 7,724,289 B2* | 5/2010 | Kudo | 348/231.2 |
| 7,904,824 B2* | 3/2011 | Stern et al. | 715/771 |
| 2004/0026997 A1* | 2/2004 | Kim | 307/9.1 |
| 2006/0007469 A1* | 1/2006 | Uruma | 358/1.14 |
| 2006/0169907 A1* | 8/2006 | Shinden | 250/370.09 |
| 2006/0212104 A1* | 9/2006 | Hindinger et al. | 607/150 |
| 2007/0140424 A1 | 6/2007 | Serceki | |
| 2008/0119731 A1* | 5/2008 | Becerra et al. | 600/437 |
| 2008/0240358 A1 | 10/2008 | Utschig et al. | |
| 2008/0309879 A1* | 12/2008 | Hirji | 351/223 |
| 2009/0129547 A1* | 5/2009 | Jabri et al. | 378/115 |
| 2009/0190718 A1 | 7/2009 | Fan | |
| 2009/0281497 A1* | 11/2009 | Kamen et al. | 604/151 |
| 2010/0168576 A1* | 7/2010 | Poland et al. | 600/443 |
| 2011/0254563 A1* | 10/2011 | Liu et al. | 324/538 |
| 2012/0085174 A1* | 4/2012 | Urbano et al. | 73/602 |
| 2012/0203177 A1* | 8/2012 | Lanier et al. | 604/151 |

OTHER PUBLICATIONS

Unofficial translation of Japanese Office Action for Japanese Application No. 2010-190203 dated Jan. 8, 2014.

* cited by examiner

MULTIFUNCTIONAL SWITCH AND DETECTOR ASSEMBLY FOR A MEDICAL IMAGING SYSTEM INCLUDING THE SAME

BACKGROUND OF THE INVENTION

The subject matter disclosed herein relates generally to imaging detectors, and more particularly to a circuit for performing multiple functions on a portable imaging detector.

In various medical imaging applications, a portable imaging detector may be utilized to perform medical imaging. At least one conventional portable x-ray detector includes an external casing that is typically formed of metal. The external casing includes a front cover, a back cover, and a plurality of sides that together form the external casing. The portable x-ray detector also includes a plurality of detector elements that are disposed proximate to the portable x-ray device front cover. During operation, x-rays pass through the front cover and impinge on the plurality of detector elements. The detector elements produce an electrical signal that represents the intensity of the impinging X-ray beam and hence allows estimation of the attenuation of the beam as the beam passes through the object.

At least one conventional portable detector utilizes a cable or tether to connect the portable detector to an imaging system. The imaging system then provides power and communication to the portable detector utilizing the tether. During operation, the imaging system energizes and de-energizes the portable detector by transmitting a power signal through the tether to the portable detector. Another conventional portable detector includes a battery to provide power to operate the detector. To make the portable detector lightweight, the capacity of the battery is limited. Thus, the amount of time that the detector can be operated on a single battery charge is also limited.

During an imaging operation, the portable detector is fully energized to enable the imaging system to receive imaging data from the portable detector. However, when the portable detector is not being used in to perform the imaging operation, the portable detector remains fully energized to enable the imaging system to communicate with the portable detector. As such, the power consumed by the portable detector is substantially the same whether the portable detector is being used to actively image a patient or when the portable detector is not being actively used to image the patient. As a result, the life of the battery is continuously reduced in both modes of operation. Therefore, the battery may not be fully charged when the detector is required to perform imaging operations. Moreover, additional batteries may be required thus increasing the cost of operating the portable detector.

BRIEF DESCRIPTION OF THE INVENTION

In one embodiment, a portable detector control circuit for reducing power consumption of a portable x-ray detector is provided. The detector control circuit includes a multi-function switch coupled to the portable detector, and a detector control module installed in the portable detector, the detector control module receiving an input from the multi-function switch and based on the received input reconfiguring the portable detector from a first operational mode to a different second operational mode.

In another embodiment, a portable detector is provided. The portable detector includes a detector array and a detector control circuit coupled to the detector array. The detector control circuit includes a multi-function switch coupled to the portable detector, and a detector control module installed in the portable detector, the detector control module receiving an input from the multi-function switch and based on the received input reconfiguring the portable detector from a first operational mode to a different second operational mode.

In a further embodiment, a method for operating a portable detector is provided. The method includes providing a multi-function switch configured to couple to the portable detector, providing a detector control module configured to be installed in the portable detector, the detector control module, and operating the multi-function switch to enable the detector control module to reconfigure the portable detector from a first operational mode to a different second operational mode.

In a still further embodiment, a medical imaging system is provided. The medical imaging system includes a gantry, an x-ray source coupled to the gantry, an x-ray system controller for operating the x-ray source, a plurality of portable x-ray detector arrays, and a control circuit coupled to the plurality of portable x-ray detector arrays. The control circuit includes a multi-function switch coupled to the portable medical imaging system detector, and a detector control module installed in the portable medical imaging system detector, the detector control module receiving an input from the multi-function switch and based on the received input reconfiguring at least one of the portable x-ray detector arrays from a first operational mode to a different second operational mode.

DETAILED DESCRIPTION OF THE INVENTION

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate, or are configured to generate, at least one viewable image.

Figure 1:
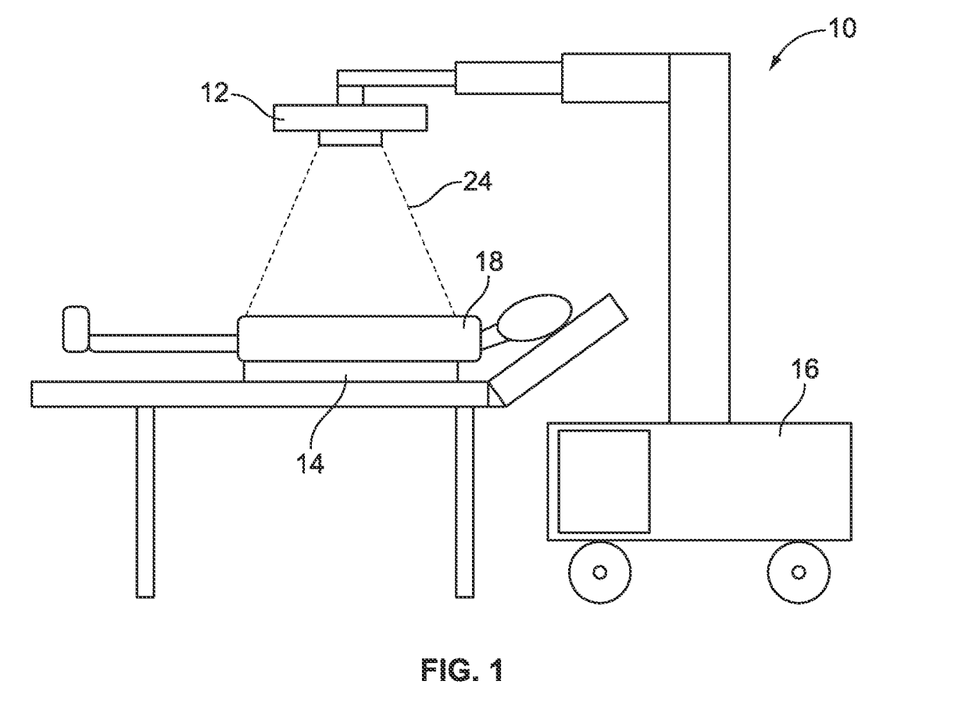
FIG. 1 is a pictorial view of an exemplary medical imaging system in accordance with an embodiment of the present invention.
Figure 2:
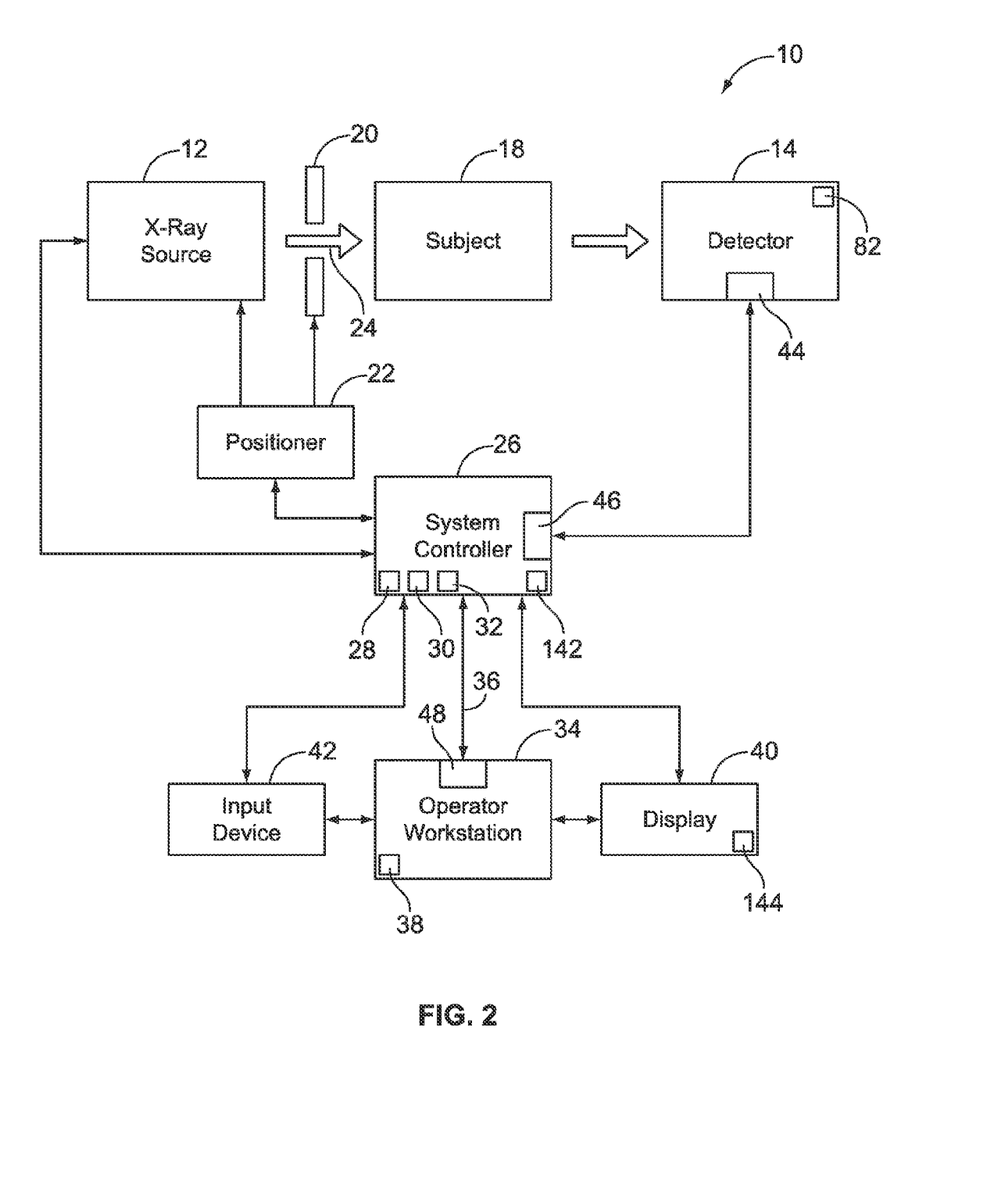
FIG. 2 is a block schematic diagram of the exemplary medical imaging system shown in FIG. 1 in accordance with an embodiment of the present invention.

Referring to the drawings, FIG. 1 is a pictorial view of an exemplary imaging system 10 in accordance with an embodiment of the present invention. FIG. 2 is a block schematic diagram of the exemplary imaging system 10 shown in FIG. 1 in accordance with an embodiment of the present invention. Various embodiments of the invention may be used with the exemplary medical imaging system 10 as shown in FIGS. 1 and 2. The medical imaging system 10 may be any type imaging system, for example, different types of medical imaging systems, such as an x-ray imaging system, a tomosynthesis imaging system, a Positron Emission Tomography (PET), a Single Photon Emission Computed Tomography (SPECT), a Computed Tomography (CT), an ultrasound system, Magnetic Resonance Imaging (MRI) or any other system capable or generating medical images. Moreover, the various embodiments are not limited to medical imaging systems for imaging human subjects, but may include veterinary or non-medical systems for imaging non-human objects, or non-destructive testing systems (e.g. airport baggage systems) etc.

The medical imaging system 10 in the preferred embodiment is a digital radiography imaging system 10 that includes an x-ray source 12 and a detector 14. As shown in FIG. 1, the x-ray source 12 is mounted to a gantry 16. In the exemplary embodiment, the gantry 16 is movable to enable the x-ray source 12 to be properly positioned with respect to a subject 18 being imaged or to enable the x-ray source 12 to be moved from one imaging room to another. Optionally, the gantry 16 is stationarily mounted by coupling the gantry to a floor, for example. Referring to FIG. 2, the imaging system 10 may also include a collimator 20 that is disposed between the x-ray source 12 and the subject 18. The imaging system 10 may also include a positioner 22. The positioner 22 is a mechanical controller coupled to the x-ray source 12 and collimator 20 for controlling the positioning of the x-ray source 12 and the collimator 20.

During operation, the imaging system 10 generates images of the subject 18 by means of an x-ray beam 24 emitted by the x-ray source 12, and passing through the collimator 20. The collimator 20 forms and confines the x-ray beam 24 to a desired region, wherein the subject 18, such as a human patient, an animal or an object, is positioned. A portion of the x-ray beam 24 passes through or around the subject 18 and, being altered by attenuation and/or absorption by tissues within the subject 18, continues on toward and impacts the detector 14. In one embodiment, the detector 14 may be a fixed detector that is mounted in a fixed position. In the exemplary embodiment, the detector 14 is a portable digital flat panel x-ray detector. During operation, the detector 14 converts x-ray photons received on its surface to lower energy light photons, and subsequently to electric signals, which are acquired and processed to reconstruct an image of internal anatomy of the subject 18.

The imaging system 10 further includes a system controller 26 coupled to the x-ray source 12, the detector 14, and the positioner 22 for controlling operation of the x-ray source 12, the detector 14, and the positioner 22. The system controller 26 may supply both power and control signals for imaging examination sequences. In general, the system controller 26 controls the operation of the imaging system to execute examination protocols and to process acquired image data. The system controller 26 may also include signal processing circuitry, based on a general purpose or application-specific computer, associated memory circuitry for storing programs and routines executed by the computer, as well as configuration parameters and image data, interface circuits, and so forth.

The system controller 26 may further include at least one computer or processor 28 that is configured to coordinate the operation of the x-ray source 12, the detector 14, and the positioner 22, and to process image data acquired from the detector 14. As used herein, the term "computer" may include any processor or processor-based system including systems using controllers, reduced instruction set circuits (RISC), application specific integrated circuits (ASICs), logic circuits, and any other circuit or processor capable of executing the functions described herein. The above examples are exemplary only, and are thus not intended to limit in any way the definition and/or meaning of the term "computer". During operation, the processor 28 carries out various functionality in accordance with routines stored in an associated memory circuitry 30. The associated memory circuitry 30 may also serve to store configuration parameters, imaging protocols, operational logs, raw and/or processed image data, and so forth.

The system controller 26 may further include interface circuitry 32 that permits an operator or user to define imaging protocols, imaging sequences, determine the operational status and health of system components, and so-forth. The interface circuitry 32 may allow external devices to receive images and image data, and command operation of the radiography system, configure parameters of the system, and so forth.

The system controller 26 may be coupled to a range of external devices via a communications interface. Such devices may include, for example, an operator workstation 34 for interacting with the system controller 26 or directly to the imaging system, processing or reprocessing images, viewing images, and so forth. The operator workstation 34 may be embodied as a personal computer (PC) that is positioned near the imaging system 10 and hard-wired to the system controller 26 via a communication link 36. The workstation 34 may also be embodied as a portable computer such as a laptop computer or a hand-held computer that transmits information to the system controller 26. In one embodiment, the communication link 36 may be hardwired between the system controller 26 and the workstation 34. Optionally, the communication link 36 may be a wireless communication link that enables information to be transmitted to or from the workstation to the system controller 26 wirelessly. In the exemplary embodiment, the workstation 34 controls real-time operation of the imaging system 10. The workstation 34 is also programmed to perform medical image diagnostic acquisition and reconstruction processes described herein.

Accordingly, the operator workstation 34 includes a central processing unit (CPU) or computer 38, a display 40 and an input device 42. In the exemplary embodiment, the computer 38 executes a set of instructions that are stored in one or more storage elements or memories, in order to process input data. The storage elements may also store data or other information as desired or needed. The storage element may be in the form of an information source or a physical memory element within the computer 38. The set of instructions may include various commands that instruct the computer or processor 38 as a processing machine to perform specific operations such as the methods and processes of the various embodiments described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

The CPU 38 connects to the communication link 36 and receives inputs, e.g., user commands, from the input device 42. The input device 42 may be, for example, a keyboard, mouse, a touch-screen panel, and/or a voice recognition system, etc. Through input device 42 and associated control panel switches, the operator can control the operation of the imaging system 10 and the positioning of the x-ray source 12 for a scan. Similarly, the operator can control the display of the resulting image on the display 40 and can perform image-enhancement functions using programs executed by the workstation CPU 38. The workstation 34 may also be linked to the system controller 26 by any one or more network links.

In the exemplary embodiment, to transmit the electric signals from the detector 14 to the system controller 26 or the workstation 34, the detector 14 includes a transceiver 44 that is configured to transmit the electrical signals and other information generated by the detector 14 in a wireless format to a corresponding transceiver 46 that is mounted in the system controller 26. Optionally, the transceiver 44 is configured to transmit the electrical signals and other information generated by the detector 14 in a wireless format to a corresponding transceiver 48 that is mounted in the workstation 34.

Figure 3:
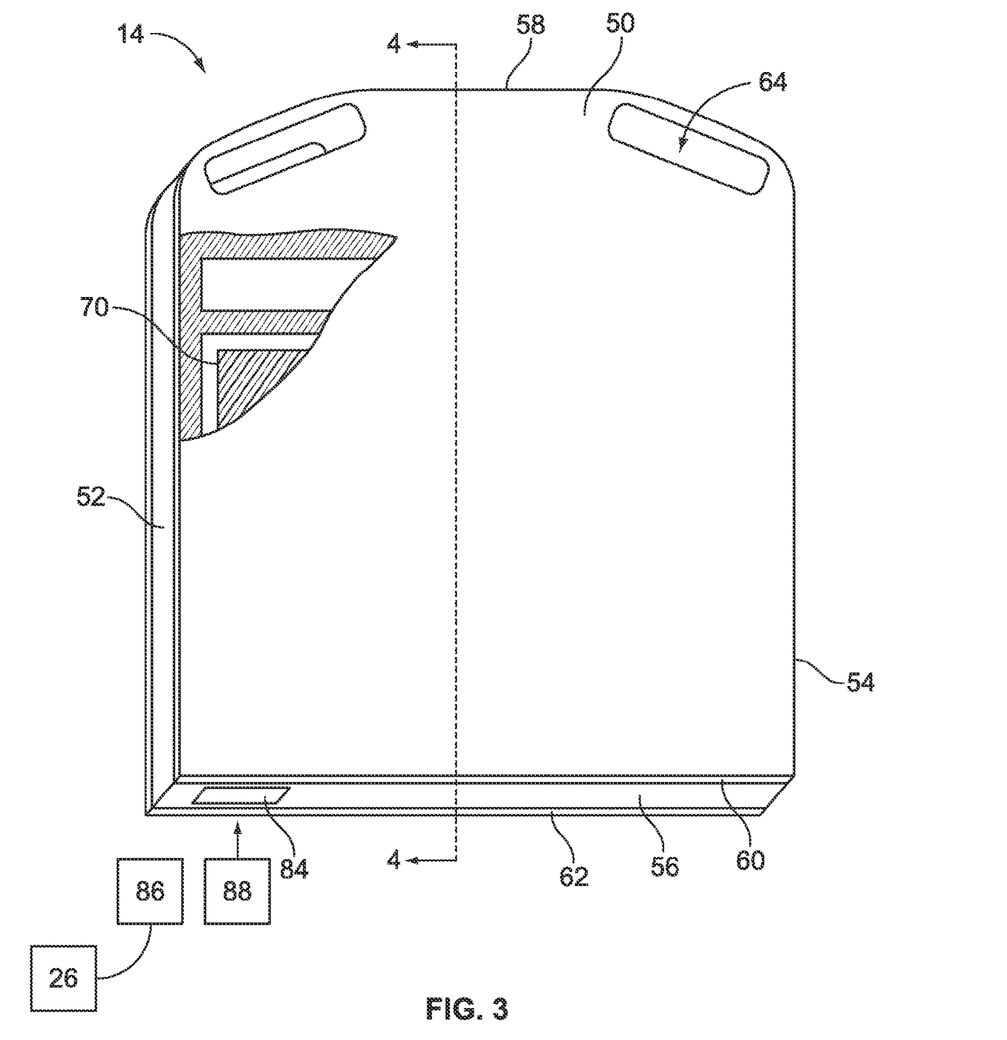
FIG. 3 is a top cut-away view of the exemplary x-ray detector shown in FIGS. 1 and 2 in accordance with an embodiment of the present invention.

FIG. 3 is a bottom cut-away view of the exemplary portable detector 14 shown in FIGS. 1 and 2. In the exemplary embodiment, the portable detector 14 is hand-carried by an operator to various locations to perform medical imaging. Additionally, the portable detector 14 may be mounted on a wheeled cart or other movable apparatus to enable an operator to move the detector 14 from one location to another location.

As shown in FIG. 3, the portable detector 14 includes a casing 50. The casing 50 is formed to include a pair of sidewalls 52 and 54, a bottom side 56, and an opposing top side 58. The casing 50 also includes a front cover 60, shown as a surface parallel to the plane of the illustration, and an opposing back cover 62. The casing also includes a handle 64 that extends from the front cover 60 to the back cover 62. During operation, the handle 64 enables an operator to transport the portable detector 14. Specifically, the handle 64 can be used to mount, carry and/or store the portable detector 14. The sidewalls, top and bottom walls, the front and back covers together form the casing 50. The casing 50 may be made of a lightweight, low atomic number (N) material, such as aluminum, or a graphite material. Graphite has a lower weight than aluminum, but it is also stiffer and less energy-absorbent.

Figure 4:
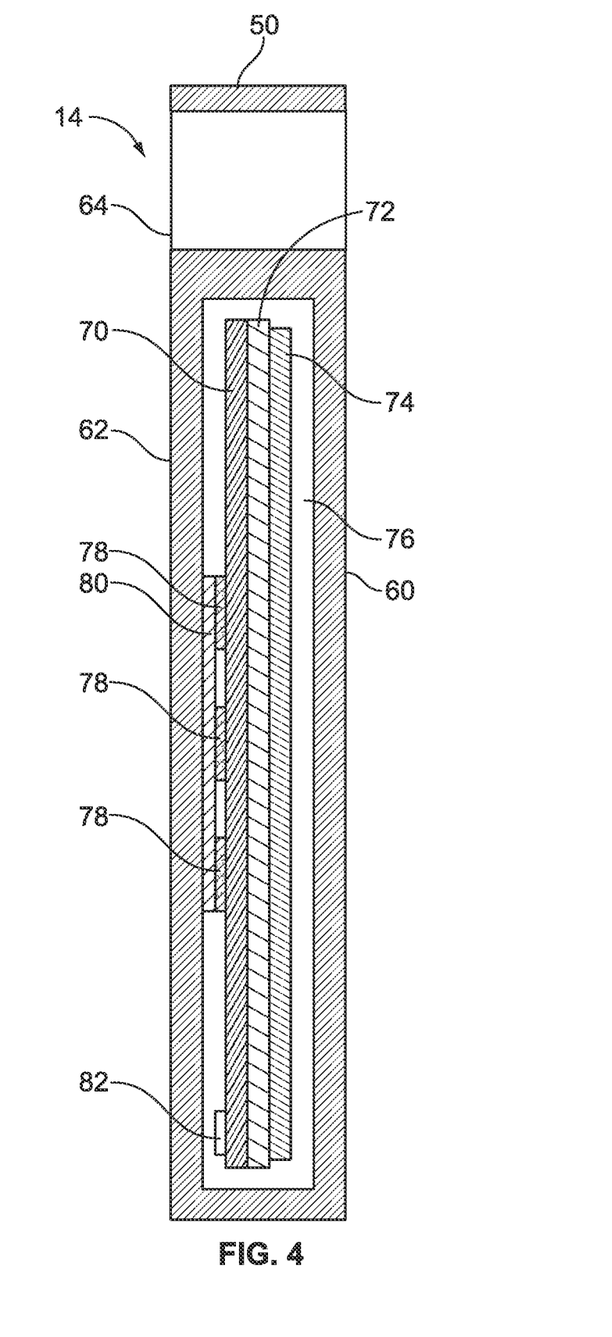
FIG. 4 is a side cut-away view of the detector shown in FIG. 3.

FIG. 4 is a side cut-away view of the portable detector 14 shown in FIG. 3 viewed along the line 4-4 of FIG. 3. As shown in FIG. 4, the detector 14 also includes a circuit board 70 that is affixed to a panel support 72 that may be fabricated from a low N material, which in turn is affixed (e.g., using an adhesive) to a panel 74. The panel 74 may be a glass panel and may include x-ray scintillator material. In the exemplary embodiment, the panel 74 includes a scintillator. As such, during operation, the panel 74 is formed to include a plurality of detector rows that each includes a plurality of detector elements (not shown), that together sense the projected x-rays that pass through an object, such as a patient. During operation, each detector element produces an electrical signal that represents the intensity of an impinging X-ray beam and hence allows estimation of the attenuation of the beam as the beam passes through the subject 18. In some embodiments, the panel support 72 is not used, and circuit board 70 is affixed directly to the panel 74. Together, circuit board 70 and panel 74 (and panel support 72, if present) comprise an "electronic assembly."

To provide some degree of break resistance for panel 74, a gap 76 is provided between the panel 74 and the front cover 60. Also, the electronic assembly is clear of any wall of the casing, but is mounted to the back cover 62. Additionally, heat generating components 78 on the circuit board 70 may be thermally coupled to back cover 62 using a heat conducting compound 80. The heat conducting compound 80 provides, directly or indirectly, a mechanical coupling between the circuit board 70 and the back cover 62. In the exemplary embodiment, the portable detector 14 also includes a processor 82. In the exemplary embodiment, the processor 82 is mounted to the circuit board 70. The processor 82 is configured to store information to operate the portable detector 14 and/or to transmit information to a remote location via the wireless transceiver 34 as discussed above.

In the exemplary embodiment, the detector 14 is portable, but typically large enough to image a significant region of a human patient, such as a patient's chest. Thus, the portable detector 14 may be only about one or a few centimeters in thickness, but may be tens of centimeters in width and length. In one embodiment, the portable detector 14 also includes an x-ray grid or anti-scatter grid, or some other grid appropriate for medical x-ray imaging. Referring again to FIG. 3, the portable detector also includes a receptacle 84 that is configured to receive either a tether 86 or a battery 88. The tether 86 is embodied as a hardwired cable that enables a remote station such as, the controller 26 to provide power to and communicate with the portable detector 14. Optionally, the portable detector 14 may be operated using the battery 88 and communicate with a remote station via the wireless links discussed above.

Figure 5:
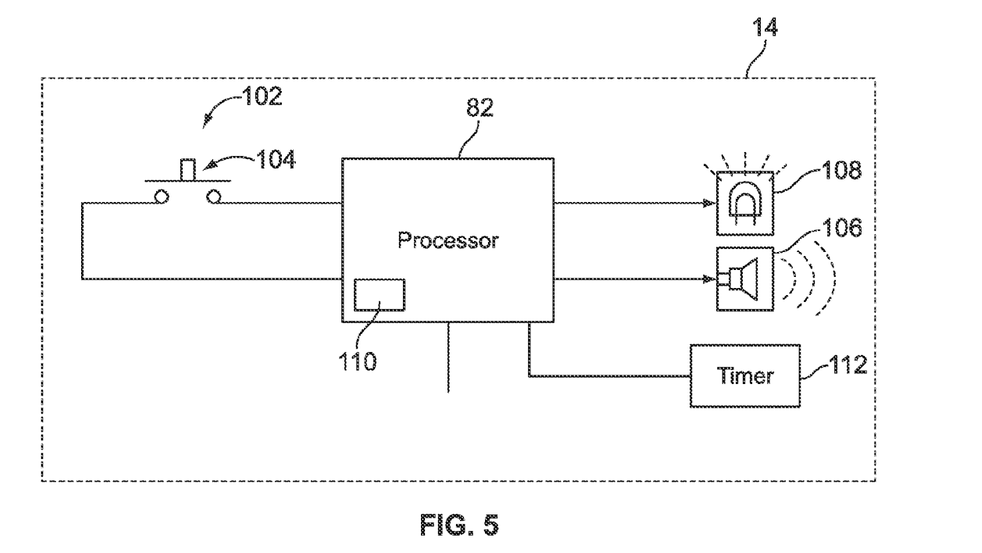
FIG. 5 is a schematic illustration of an exemplary power control circuit that may be used with the detector shown in FIGS. 1-4 in accordance with an embodiment of the present invention.

To become familiar with the problems associated with conserving power in a portable detector, such as the detector 14 shown in FIGS. 1-4, reference is now made to FIG. 5. FIG. 5 is a schematic illustration an exemplary detector control circuit 100. During operation, the detector control circuit 100 is configured to enable an operator to modify the power being consumed by the detector by switching the detector to various operational modes. The various operational modes enable the portable detector to conserve energy and therefore extend the life of the battery.

Figure 6:
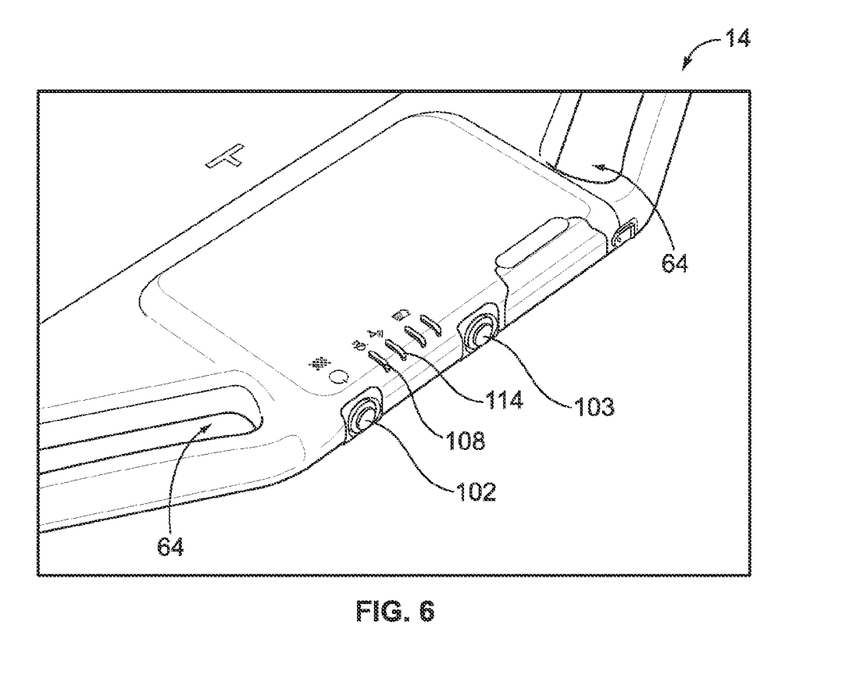
FIG. 6 is a top perspective view of a portion of the detector shown in FIGS. 1-4 in accordance with an embodiment of the present invention.

As shown in FIG. 5, the detector control circuit 100 includes a multi-function switch 102 that is coupled to a processor such as the processor 82 shown in FIG. 2. In the exemplary embodiment, the multi-function switch 102 is embodied as a pushbutton switch that is actuated by depressing and releasing a button 104 on the switch 102. The multi-function switch may include a spring mechanism (not shown) that biases the switch 102 in an "out", "unpressed" or "deactivated" position such that a current flow through the switch is terminated. When the button 104 is depressed the switch enables current to flow therethrough. Optionally, the multi-function switch 102 may be embodied as a spring-loaded selector switch, a toggle switch, a joystick, or other types of switches such as a touchscreen switch. As shown in FIG. 6, the multi-function switch 102, in the exemplary embodiment, is located proximate to the detector handle 64. Positioning the multi-function switch 102 proximate to the detector handle 64 enables the operator to grasp the handle 64 and simultaneously operate the multi-function switch 102. Optionally, the multi-function switch 102 may be installed at other locations on the detector 14.

Referring again to FIG. 5, the detector control circuit 100 also includes an audible indicator 106 and a visual indicator 108. The audible indicator may be embodied as a speaker for example. The visual indicator 108 may be embodied as a light emitting diode (LED). During operation, the processor 82 transmits signals to each of the audible indicator 106 and the visual indicator 108 to activate each device.

The detector control circuit 100 further includes a detector control module 110. The detector control module 110 may be implemented as a software program that is installed on the processor 82. Optionally, the detector control module 110 may be implemented as a hardware device such as an application specific integrated circuit (ASICs), a logic circuit, or any other circuit or processor capable of executing the functions described herein. During operation, the detector control module 110 is configured to utilize a signal received from the multi-function switch to reconfigure the detector 14 in different modes of operation to reduce power consumption and perform other functions as described in further detail below. The detector control circuit 100 also includes a timer 112. The operation of the timer 112 is discussed below.

Figure 7:
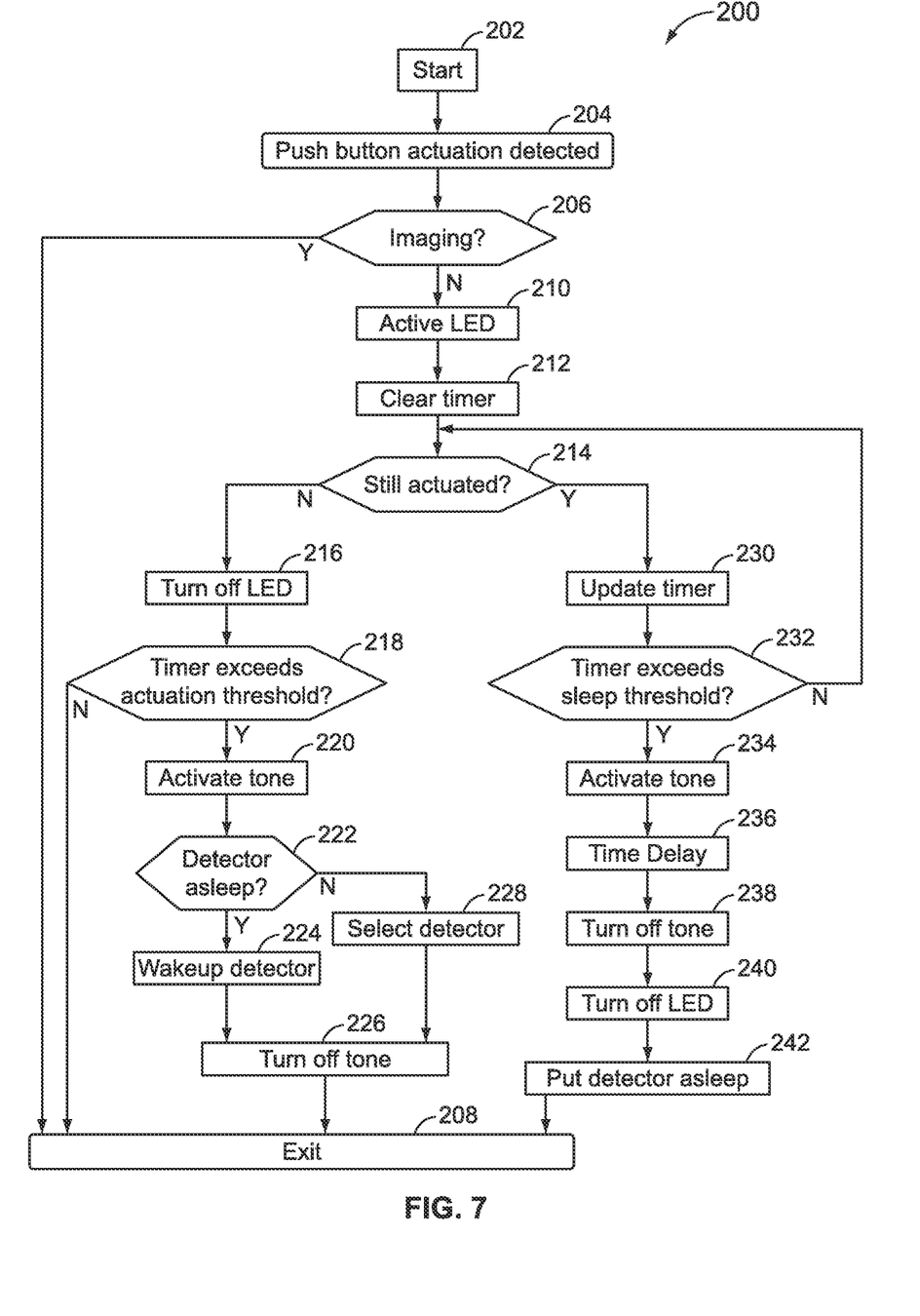
FIG. 7 is a flowchart of an exemplary method of operating the power control circuit shown in FIG. 5.

FIG. 7 is a flowchart of an exemplary method 200 of operating the detector control circuit 100. As discussed above, to conserve power consumption, the detector 14 is configured to operate in a plurality of operational modes. One such operation mode includes the detector sleep mode. In the detector sleep mode, the multi-function switch 102 is operated such that power is supplied to the multi-function switch 102 itself and the processor 82. In the sleep mode, power is not supplied to either the transceiver 44 or the detector electronics, e.g. the panel 74. In the sleep mode, power is conserved by deactivating components that consume the majority of power while the remaining components, e.g. the multi-function switch and the processor 82 remain activated to enable the operator to operate the multi-function switch and thus to configure the detector in other modes as discussed below.

The multi-function switch 102 is also configured to enable an operator to "wake up" the detector 14 from sleep mode and configure the detector 14 in an "active" or "idle" mode. In the idle mode, the multi-function switch 102 is operated such that power is supplied to the multi-function switch 102, the processor 82, the transceiver 44, and the detector electronics, e.g. the panel 74. In the idle mode, the detector 14 is configured to communicate with a remote station, such as the system controller 26 and/or the workstation 34.

The multi-function switch 102 is also configured to enable an operator to configure the detector 14 in a "detector select mode". In the detector select mode, the multi-function switch 102 is operated such that power is supplied to the multi-function switch 102, the processor 82, the transceiver 44, and the detector electronics, e.g. the panel 74. In the detector select mode, the detector 14 is configured to communicate with a remote station, such as the system controller 26 and/or the workstation 34. Moreover, in the detector select mode, a signal is transmitted from the detector 14 to either the system controller 26 and/or the workstation 34. The signal represents to the imaging system that this specific detector has been selected for imaging. For example, the imaging system 10 may include multiple detectors 14. Some of the detectors 14 may be configured in the "sleep mode", some may be configured in the "active mode", however only a single detector 14 is selected at one time to perform imaging. More specifically, the imaging system 10 is configured to expose and perform imaging operations using only a single detector. Therefore, the multi-function switch 102 enables the system operator to select which detector 14 is to be used for imaging. In this manner the system 102, while communicating with multiple detectors is made aware which specific detector is to be utilized to perform imaging. Optionally, the detector 14 may include at least one additional switch 103 that performs a portion of the functions described above with respect to the multi-function switch 102. More specifically, the detector 14 includes a single multi-function switch 102. Optionally, the detector 14 may include at least one additional switch that performs a portion of the functionality of the multi-function switch 102 or different functions. For example, the switch 103 may be used by the operate to configure the detector 14 in the detector select mode whereas the multi-function switch 102 is used by the operator to configure the detector in either the sleep mode or the idle mode. Utilizing a second switch 103 enables the operator to select a detector for exposure from a number of detectors that are present rather than having to move to the x-ray system console. The switches 102 and 103 may be embodied as a fingerprint reader on the detector 14, an RFID sensor in the detector 14, a bar-code reader in the detector 14, a sensor for a hand-held remote which is separate from the detector 14, but not located on the console, or some other sort of proximity detection, such as a Hall effect switch.

Referring again to FIG. 7, at 202, the detector 14 is operating in the idle mode as defined above. At 204, the detector control module 110 determines if the multi-function switch 102 has been activated by pushing the button 104. If the button 104 is pushed the method proceeds to 206, otherwise no actions are taken. At 206, the detector control module 110 determines if the detector 114 is operating in the detector selected mode. If the detector 14 is currently being utilized by the imaging system 10 to perform imaging, the detector control module 110 proceeds to step 208 and the program is terminated. Step 206 allows the detector control module 110 to determine if the button 104 has been depressed inadvertently by the operator while the detector 14 is currently in the detector select mode and thus enabled for imaging. More specifically, if the detector 14 is currently being used for imaging, the detector control module 110 takes no further action. If the detector 14 is not currently imaging, the detector control module 110 proceeds to step 210

At 210, the detector control module 110 activates the visual indicator 108. The visual indicator 108 is utilized to inform an operator that the button 104 is being depressed, thus informing the operator that the detector 14 is being reconfigured.

At 212, the detector control module 110 activates the timer 112 (shown in FIG. 5). The timer 112 is utilized to determine the length of time the operator is depressing the button 104.

At 214, the detector control module 110 determines if the button 104 is still being depressed. For example, during operation, the operator, once observing the visual indicator 108 has been activated at step 210, may choose to release the button 104 or may choose to continue depressing the button 104. If the operator chooses to release the button 104, the detector control module 110 at step 214 determines that the button 104 is not being depressed and proceeds to step 216, optionally, if the button 104 is still being depressed, the detector control module 110 proceeds to Step 230 which is discussed below.

At 216, the detector control module 110 deactivates the visual indicator 108 to inform the operator that the button 104 is no longer being depressed.

At 218, the detector control module 110 determines the length of time that the button 104 was depressed using information from the timer 112. As discussed above, at step 212, the timer 112 is activated when the operator depresses the button 104. At step 218, the detector control module 110 determines the length of time that the button 104 was depressed. If the button 104 was depressed for a first amount of time that does not exceed a predetermined threshold, the detector control module 110 proceeds to step 208 and the program is terminated. The predetermined threshold is selected to ensure that the button 104 has not been inadvertently depressed. For example, if the button 104 has been inadvertently depressed by the operator for a relatively short time, the time will not exceed the predetermined threshold and the program is terminated. Optionally, if the button 104 has been depressed for an amount of time that is sufficient to exceed the predetermined threshold, indicating that the operator desires to change the configuration of the detector 14, the detector control module 110 proceeds to step 220.

At 220, the detector control module 110 activates the audible device 106 such that an audible tone is emitted. The audible tone provides an audible indication or acknowledgement to the operator that the button 104 has been depressed a sufficient amount of time to enable the detector 14 to be reconfigured. Optionally, the detector 14 may emit a visual indication that the button 104 has been depressed a sufficient amount of time to reconfigure At 222, the detector control module 110 determines if the detector 14 is in the sleep mode. If the detector control module 110 determines that the detector 14 is operating in the sleep mode, the detector control module 110 proceeds to Step 224.

At 224, the detector control module 110 reconfigures the detector 14 from the sleep mode to the idle mode to "wakeup" the detector 14. In this mode, the detector communications and electronics portions are activated At 226, after the communications and detector electronics are activated, the detector control module 110 is configured to deactivate the audible device 106 to terminate the audible tone. Terminating the audible tone provides an audible acknowledgement to the operator that the detector 14 has been configured in the idle mode. This can be confirmed visually by observing that the detector 14 is communicating with the imaging system by observing that a communication LED 116 (shown in FIG. 6) is green or yellow indicating that communication is established between the detector and the imaging system. Green indicates a strong communication link has been established between the detector 14 and a remote station. Yellow indicates that a weaker communication link is established between the detector 14 and the remote station. Red indicates that no communication link has been established. It should be realized that other colors may be utilized.

Referring again to FIG. 7, at Step 222, if the detector control module 110 determines that the detector 14 is not in the sleep mode, that is the detector 14 is currently in the idle mode, the detector control module 110 reconfigures the detector 14 to operate in the detector selected mode. The detector control module 110 then deactivates the audible device 106 to terminate the audible tone. Deactivating the audible tone provides an audible acknowledgement to the operator that the detector 14 has been activated.

Referring again to Step 214, if the detector control module 110 determines that the button 104 is still being depressed, the method proceeds to Step 230. At 230, the detector control module 110 determines the quantity of time that the button 104 was depressed using information from the timer 112. As discussed above, at step 212, the timer 112 is activated when the operator depresses the button 104. At step 230, the detector control module 110 determines the length of time that has elapsed since the button 104 was initially depressed.

At 232, the detector control module 110 determines if the quantity of time determined in Step 230 exceeds a predetermined threshold. If the button 104 was depressed for a first amount of time that does not exceed the predetermined threshold, the detector control module 110 proceeds to step 214. It should be realized that during this operation, the program functions as a loop. That is, while the button 104 is still being depressed, the timer 112 at step 232 will continually revert back to step 214 to determine if the button 104 is still being depressed. Once the time the button 104 is being depressed exceeds the predetermined threshold in Step 232, the detector control module 110 proceeds to Step 234.

At 234, the detector control module 110 activates the audible indicator 106. The tone emitted form the audible indicator 106 provides an audible indication or acknowledgement to the operator that the button 104 has been depressed a sufficient amount of time to reconfigure the detector 14.

At 236, the detector control module 110 activates the timer 112 to keep the audible indicator 106 emitting the audible indication for a predetermined quantity of time. When the predetermined length of time has elapsed the detector control module 110 proceeds to Step 238. At Step 238, the detector control module 110 deactivates the audible indicator 106 and thus terminates the audible indication. At 240, the detector control module 110 deactivates the visual indicator 108 to inform the operator that the operation is completed. At 242, the detector control module 110 reconfigures the detector 114 in the sleep mode and the program is then terminated at Step 208.

Described herein is a portable detector 14 that includes a detector control circuit 100. The detector control circuit 100 includes a multi-function switch 102 that is coupled to a processor such as the processor 82 shown in FIG. 2. In the exemplary embodiment, the multi-function switch 102 is embodied as a pushbutton switch that is actuated by depressing and releasing a button 104 on the switch 102. During operation, the while the multi-function switch 102 is depressed, the detector control module 110 senses the status change of the switch which is then indicated to the operator through a visible indicator, such as an LED. The detector control module then performs the requested operation and confirms the completion of the operation through an audible indicator. As such, the multi-function switch 102 performs multiple functions. One such function is to control detector power by waking up the detector and placing the detector back in sleep mode when the detector is not being utilized.

Another function is to enable the operator to select a specific detector for imaging when multiple detectors are connected to the imaging system in a wireless arrangement. This function allows the operator to select the detector in a convenient fashion without requiring the operator to interact with the system console, which may be in another room. This function also improves both workflow and efficiency while reducing human error.

Accordingly, described herein is a portable x-ray detector that is both lightweight, wireless, and rugged. Moreover, because the detector includes only a single multi-function switch, rather than multiple buttons, the reliability and ruggedness of the detector is improved. More specifically, any perforation of the outer cover of the detector represents a weak point compared to the structural integrity that a solid cover provides. Each perforation is potentially an inlet for fluid which may cause failure of the detector. More buttons represent more perforations in the cover and more opportunities for failure of either the cover or the operation of the detector. Therefore, a single multi-function switch requires only a single opening in the detector casing. Moreover, the components on the handle are waterproof to prevent patient body fluids and cleaning agents from getting inside the detector.

During operation, the multi-function switch as well as the visual and audible indicators are sensed and controlled by a microcontroller. When the microcontroller senses the pushbutton signal, it determines the corresponding actions according to the current state of the detector and the amount of time that the button is actuated. The pushbutton can be used for many different purposes. One of them is to select the detector to be imaged in multiple detector applications as shown below. The multiple detector application occurs mainly in emergency or trauma rooms. If a patient has been involved in a car accident for instance, the doctors need x-ray images covering the whole body of the patient. It is desired to place multiple detectors in place before the patient is rushed into the trauma room to save examination time and reduce the need to reposition the patient. The system needs to understand which detector will receive each x-ray exposure during the entire exam. The multi-function push button can then be used to select the detector. When the operator pushes the button, the microcontroller receives the signal and communicates to the x-ray system via wireless communication channel. Another function of the button is to wakeup the detector when it is asleep. To save battery power, the detector puts itself to sleep after a predetermined length of time of inactivity. When the detector is asleep, most of the circuits, including the wireless interface are powered off. Thus the system cannot wakeup the detector through a wireless host command. Only the microcontroller and the push button circuits remain powered and are then used for this purpose. The microcontroller and button will consume considerably less power than the wireless link inside the detector.

Consequently, powering off the wireless link while maintaining power to the microcontroller will conserve battery power while allowing the user to wakeup the detector conveniently from the detector, rather than a system console, for example. The button can also be used to switch the detector to sleep mode immediately when it will not be used for a long time. For instance, this may be desirable in a surgery room where the detector is positioned well in advance of its actual use. In order to avoid inadvertent actuation, the push button must be actuated for more than a predetermined length of time. In addition, some actions are prohibited in particular situations. For instance, switching the detector into sleep mode is prohibited during image acquisition. That is, detector will not go to sleep during image acquisition even though an operator may attempt to invoke this transition through the use of the push button.

A technical effect of the detector control circuit 100 is to reduce power consumption by enabling an operator to reconfigure the portable detector 14 into different operating modes. For example, the sleep mode enables the detector 14 to operate at a reduced power consumption. The multi-function switch then enables the operator to reconfigure the detector 14 from the sleep mode to an idle or active mode. The idle mode of detector operation consumes more power than the sleep mode. As such, the operator may reconfigure the detector in the idle mode just prior to the detector being used for imaging thus increasing the life of the battery. The detector control circuit 100 also enables an operator to select a specific detector that is to be used during the imaging operation. Accordingly, the imaging system 10 may include multiple detectors and the detector control circuit 110 enables the operator to inform the imaging system which specific detector is to be utilized to perform imaging.

Some embodiments of the present invention provide a machine-readable medium or media having instructions recorded thereon for a processor or computer to operate an imaging apparatus to perform an embodiment of a method described herein. The medium or media may be any type of CD-ROM, DVD, floppy disk, hard disk, optical disk, flash RAM drive, or other type of computer-readable medium or a combination thereof.

The various embodiments and/or components, for example, the monitor or display, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. For example, the ordering of steps recited in a method need not be performed in a particular order unless explicitly stated or implicitly required (e.g., one step requires the results or a product of a previous step to be available). While the dimensions and types of materials described herein are intended to define the parameters of the invention, they are by no means limiting and are exemplary embodiments. Many other embodiments will be apparent to those of skill in the art upon reviewing and understanding the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A control circuit for a portable medical imaging system detector, said control circuit comprising:
   a multi-function switch coupled to the portable medical imaging system detector, the multi-function switch configured to enable the portable medical imaging system to operate in a sleep mode, an idle mode, and a detector select mode;
   a detector control module installed in the portable medical imaging system detector, the detector control module receiving an input from the multi-function switch and based on the received input reconfiguring the portable medical imaging system detector to operate in at least one of the sleep mode, the idle mode, or the detector select mode; and
   a visual indicator, the visual indicator being activated when the multi-function switch is depressed for a predetermined period of time.

2. A control circuit in accordance with claim 1 wherein the detector control module is further configured to:
   determine a period of time that the multi-functions switch is depressed while the detector is operating in the idle mode; and
   reconfigure the detector to operate in the sleep mode when the determined period of time exceeds a predetermined threshold.

3. A control circuit in accordance with claim 1, wherein the detector control module is further configured to:
   receive an input from the multi-function switch:
   determine if the detector is operating in the detector select mode based on the received input; and
   activate a visual indicator when the detector is not operating in the detector select mode.

4. A control circuit in accordance with claim 1, wherein the portable medical imaging system detector consumes a first amount of power in the sleep mode and a different second amount of power in the idle mode and the detector select mode.

5. A control circuit in accordance with claim 1, further comprising a timer configured to determine an amount of time the multi-function switch is depressed, the detector control module configured to activate an audible device if the amount of time exceeds a predetermined threshold.

6. A control circuit in accordance with claim 1, further comprising an audible indicator, the audible indicator enabling an operator to determine when the portable medical imaging system detector is reconfigured from the sleep mode to at least one of the idle mode and the detector select mode.

7. A control circuit in accordance with claim 1 wherein the detector control module is further configured to:
   determine a period of time the multi-functions switch is depressed while the detector is operating in the idle mode; and
   reconfigure the detector to operate in the detector select mode when the determined period of time exceeds a predetermined threshold.

8. A portable medical imaging system detector comprising:
   an x-ray detector array; and
   a detector control circuit coupled to the x-ray detector array, the detector control circuit comprising
   a multi-function switch coupled to the portable medical imaging system detector, the multi-function switch configured to enable the portable medical imaging system to operate in a sleep mode, an idle mode, and a detector select mode;
   a detector control module installed in the portable medical imaging system detector, the detector control module receiving an input from the multi-function switch and based on the received input reconfiguring the portable medical imaging system detector to operate at least one of the sleep mode, the idle mode or the detector select mode; and
   an audible indicator, the audible indicator enabling an operator to determine when the portable medical imaging system detector is reconfigured from the sleep mode to at least one of the idle mode and the detector select mode.

9. The detector of claim 8, wherein the detector control module is further configured to:
   receive an input from the multi-function switch:
   determine if the detector is operating in the detector select mode based on the received input; and
   activate a visual indicator when the detector is not operating in the detector select mode.

10. The detector of claim 8, wherein the portable medical imaging system detector consumes a first amount of power in the sleep mode and a different second amount of power in the idle mode and the detector select mode.

11. The detector of claim 8, further comprising a timer configured to determine an amount of time the multi-function switch is depressed, the detector control module configured to activate an audible device if the amount of time exceeds a predetermined threshold.

12. The detector of claim 8, further comprising a visual indicator, the visual indicator being activated when the multi-function switch is depressed.

13. The detector of claim 8, wherein the detector control module is further configured to transmit a wireless signal from the portable medical imaging system detector to a remote workstation when the portable medical imaging system detector is configured in a select mode.

14. The detector of claim 8, wherein the detector control module is further configured to:
   determine a period of time the multi-functions switch is depressed while the detector is operating in the idle mode; and
   reconfigure the detector to operate in the detector select mode when the determined period of time exceeds a predetermined threshold.

15. A method for operating a portable medical imaging system detector, the method comprising:
   providing a multi-function switch configured to couple to the portable medical imaging system detector, the multi-function switch configured to enable the portable medical imaging system to operate in a sleep mode, an idle mode, and a detector select mode;

providing a detector control module configured to be installed in the portable medical imaging system detector;

operating the multi-function switch to enable the detector control module to reconfigure the portable medical imaging system detector to operate in at least one of the sleep mode, the idle mode, or the detector select mode;

receiving an input from the multi-function switch;

determining if the detector is operating in the detector select mode based on the received input; and activating a visual indicator when the detector is not operating in the detector select mode.

16. A method in accordance with claim 15 wherein the portable medical imaging system detector consumes a first amount of power in the sleep mode and a different second amount of power in the idle mode and the detector select mode.

17. A method in accordance with claim 15 further comprising:

determining an amount of time the multi-function switch is depressed; and activating a visual indicator when the multi-function switch is depressed for a length of time that exceeds a predetermined time; and activating an audible indicator when the detector is reconfigured from the sleep mode to at least one of the idle mode and the detector select mode.

\* \* \* \* \*